(12) United States Patent
Krsek et al.

(10) Patent No.: US 7,404,970 B2
(45) Date of Patent: Jul. 29, 2008

(54) PAIN RELIEF COMPOSITION, METHOD TO FORM SAME, AND METHOD TO USE SAME

(75) Inventors: George R. Krsek, Tucson, AZ (US); Enrique E. Durazo, Oro Valley, AZ (US)

(73) Assignee: Konec, Inc., Tucson, AZ (US)

( * ) Notice: Subject to any disclaimer, the term of this patent is extended or adjusted under 35 U.S.C. 154(b) by 423 days.

(21) Appl. No.: 10/823,885

(22) Filed: Apr. 13, 2004

(65) Prior Publication Data

US 2005/0226930 A1  Oct. 13, 2005

(51) Int. Cl.
*A61K 9/28* (2006.01)
(52) U.S. Cl. ................................. 424/474
(58) Field of Classification Search ............ 424/474
See application file for complete search history.

(56) References Cited

U.S. PATENT DOCUMENTS

| | | |
|---|---|---|
| 4,851,229 A | 7/1989 | Magruder et al. |
| 5,321,012 A | 6/1994 | Mayer et al. |
| 5,352,683 A | 10/1994 | Mayer et al. |
| 5,472,708 A | 12/1995 | Chen |
| 5,508,040 A | 4/1996 | Chen |
| 5,556,838 A | 9/1996 | Mayer et al. |
| 5,681,584 A | 10/1997 | Savastano et al. |
| 5,869,498 A | 2/1999 | Mayer et al. |
| 6,007,841 A | 12/1999 | Caruso |
| 6,124,355 A * | 9/2000 | Guittard et al. ............ 514/534 |
| 6,277,384 B1 | 8/2001 | Kaiko et al. |
| 6,635,284 B2 | 10/2003 | Mehta et al. |
| 2003/0004177 A1 * | 1/2003 | Kao et al. ................ 514/282 |

OTHER PUBLICATIONS

NOVEON™, Toxicity of the Carbopol® Resins as a Class, Polymers for Personal Care, 2001, pp. 1-3.

* cited by examiner

*Primary Examiner*—Sreeni Padmanabhan
*Assistant Examiner*—Renee Claytor
(74) *Attorney, Agent, or Firm*—Dale F. Regelman; Quarles & Brady LLP

(57) ABSTRACT

An oral dosage form which includes a bi-layer tablet consisting of an Actives Granulation layer and an Osmagen Granulation layer is disclosed. An encapsulant is disposed over that bi-layer tablet. The encapsulated bi-layer tablet includes an orally therapeutically effective dose of oxycodone in combination with dextromethorphan, where the weight ratio of oxycodone to dextromethorphan is 1:5. The oral dosage form does not include an opioid antagonist.

5 Claims, 4 Drawing Sheets

PAIN RELIEF COMPOSITION, METHOD TO FORM SAME, AND METHOD TO USE SAME

FIELD OF THE INVENTION

This invention relates to a pain relief composition, a method to form Applicants' pain relief composition, and a method to use Applicants' pain relief composition.

BACKGROUND OF THE INVENTION

Many medications are used for the treatment of pain, ranging from well known, over-the-counter compounds such as aspirin, acetaminophen, ibuprofen and other non-steroidal anti-inflammatory compounds to various opioid compounds which are dispensed under a physician's prescription. Opiates in various forms, including opium, heroine and morphine which derive from the opium poppy, have very powerful analgesic properties. Opiates have been widely used for anesthesia as well for the treatment of pain, especially where the pain is very severe.

In addition to these natural opiates, many synthetic opioids have been synthesized. Morphine is still the drug of choice, however, for management of pain at least in part due to its low cost, the ability of the drug to provide relief from pain of a variety of origins, and the vast experience with this drug. Despite its therapeutic advantages and vast experience with the drug, many pain management experts believe that morphine and other opioids are under-prescribed for patients who require long-term pain therapy.

One reason for underprescription is the risk of the side effects associated with long-term administration of opioids in general, such as development of opiate tolerance, dependence, constipation, and/or other undesirable side effects (see, e.g., Moulin et al. 1992 Can Med. Assoc. J. 146:891-7). Patients who develop opioid tolerance require increased doses to achieve a satisfactory analgesic effect, and risk the development of further undesirable side effects such as respiratory depression, which can be life threatening. Physical dependence, which is related to factors such as the dose administered and the length of the administration period, can generally only be resolved by discontinuing opioid administration, which in turn results in the onset of severely painful withdrawal symptoms. Other side effects that can be associated with administration of opioids include reduced cough reflex, bronchial spasms, nausea, vomiting, peripheral vasodilation, orthostatic hypotension, vagal impact on the heart, contraction of smooth muscles (sphincters), reduced peristaltic motility in the gastrointestinal tract (e.g., constipation), urinary retention, changes in regulation of body temperature and sleep pattern, and release of histamine, adrenalin, and anti-diuretic hormone.

The negative effects on respiratory function especially impact postoperative patients, who are particularly susceptible to depression of respiratory function. Even where the concerns regarding side effects might be outweighed by the serious need for pain relief as in terminally ill patients, many doctors still avoid prescribing opioids due to concerns of abuse of surplus medication by others in contact with the patient, or even that their frequent prescription of the drug might lead to criminal investigation.

Relieving pain by using a lower dosage of opioid(s) is desirable because such a lower dosage reduces the likelihood and/or severity of the above-recited undesirable side effects. Applicants' invention includes an oral dosage form which comprises oxycodone in combination with dextromethorphan. Using Applicants' oral dosage form and method using that oral dosage form, a tablet comprising about 5 milligrams of oxycodone, in combination with about 25 milligrams of dextromethorphan, provides the same level of pain relief as does a tablet which contains about 10 milligrams of oxycodone alone.

SUMMARY OF THE INVENTION

Applicants' invention includes an oral dosage form which includes a bi-layer tablet which includes an Actives Granulation layer and an Osmagen Granulation layer. An encapsulant is disposed over that bi-layer tablet. Applicants' encapsulated bi-layer tablet includes an orally therapeutically effective dose of oxycodone in combination with dextromethorphan, where the weight ratio of oxycodone to dextromethorphan is 1:5.

Applicants' oral dosage form does not include an opioid antagonist. By "opioid antagonist," Applicants mean a pharmacologically active compounds that blocks or reverses all of the physiological effects of an opioid. Opioid antagonists include, for example, naloxone, naltrexone, nalmephene, cyclazocine, levallorphan, and the like.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF THE PREFERRED EMBODIMENTS

This invention is described in preferred embodiments in the following description with reference to the Figures, in which like numbers represent the same or similar elements. The invention will be described as embodied in a sustained release oral dosage form which includes an Actives Granulation layer in combination with an Osmagen Granulation layer. The following description of Applicant's apparatus and method is not meant, however, to limit Applicant's invention to sustained release oral dosage forms only, as the invention herein can be applied generally to oral dosage forms which include a combination of oxycodone and dextromethorphan, and which do not include an opioid antagonist.

The oral pharmaceutical compositions containing the inventive combination of drugs set forth herein may be in the form of tablets, liquids, troches, lozenges, aqueous or oily suspensions, multiparticulate formulations including dispersable powders, granules, matrix spheroids or coated inert beads, emulsions, hard or soft capsules or syrups or elixirs, microparticles (e.g., microcapsules, microspheres and the like), buccal tablets, etc. The dosage forms of the present invention may include any desired pharmaceutically acceptable excipients known to those skilled in the art.

Applicants' dosage forms may further provide an immediate release of oxycodone and dextromethorphan. In certain preferred embodiments, the dosage forms provide a sustained release of oxycodone and dextromethorphan, and provide the part or all of the dose of oxycodone and dextromethorphan in (i) immediate release form, (ii) sustained release form, or (iii) both immediate and sustained release form. Such embodiments may further comprise a portion of the oxycodone and dextromethorphan in immediate release form. Sustained release may be accomplished in accordance with formulations/methods of manufacture known to those skilled in the art of pharmaceutical formulation, e.g., via the incorporation of a sustained release carrier into a matrix containing the combination of oxycodone and dextromethorphan; or via a sustained release coating of a matrix containing the combination of oxycodone and dextromethorphan.

Figure 4:
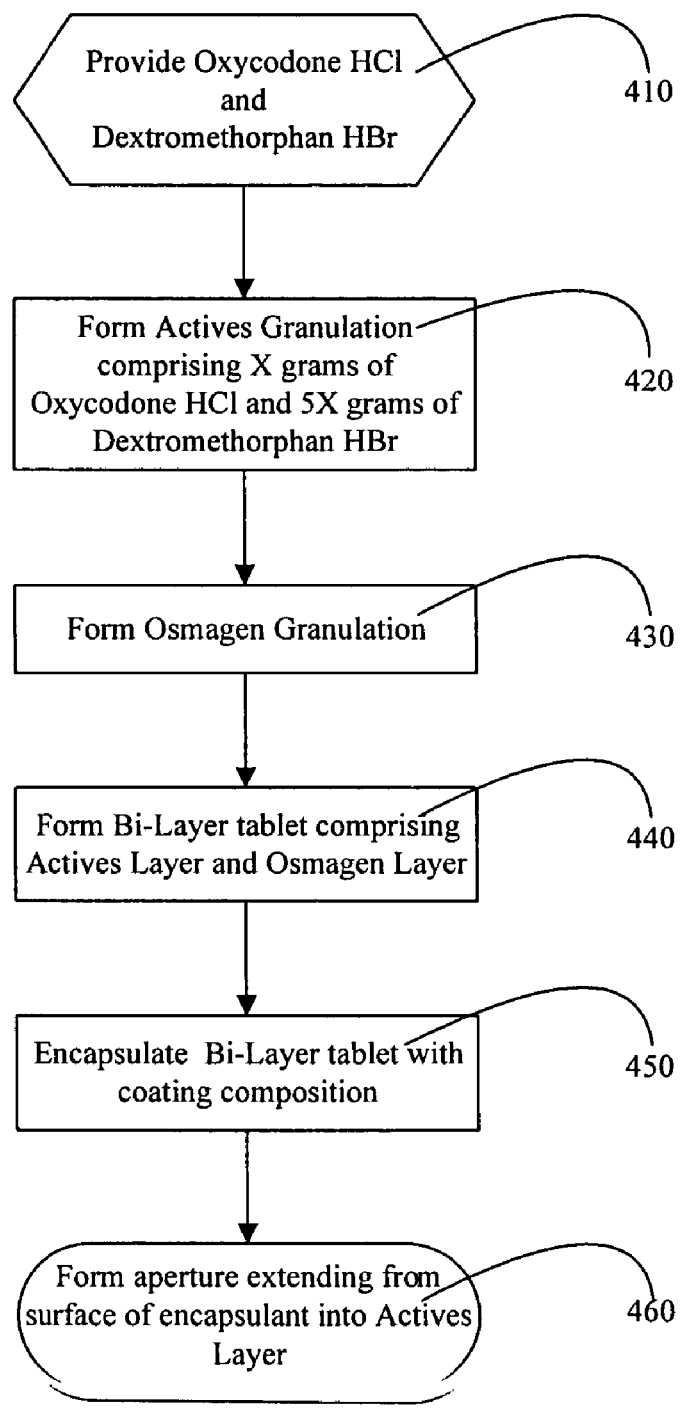
FIG. 4 is a flow chart summarizing the steps of Applicants' method to form the oral dosage form of FIG. 3.

FIG. 4 summarizes Applicants' method to form a sustained relief embodiment of their oral dosage form. Referring now to FIG. 4, in step 410 the method provides oxycodone. For purposes of the present invention, the term "oxycodone" includes the base compound, pharmaceutically acceptable salts thereof, such as for example the hydrochloride, stereoisomers thereof, ethers and esters thereof, and mixtures thereof. Step 410 further includes providing dextromethorphan. For purposes of the present invention, the term "dextromethorphan" includes the base compound, pharmaceutically acceptable salts thereof, such as for example the hydrobromide, stereoisomers thereof, ethers and esters thereof, and mixtures thereof.

In step 420, Applicants' method forms an Actives Granulation comprising oxycodone and dextromethorphan, wherein the weight ratio of oxycodone to dextromethorphan is about 1:5. Applicants evaluated various ratios of oxycodone and dextromethorphan using what is sometimes referred to as the acetic acid writhing test. See, Collier, et al., Br. Journal of Pharmacol. Chemotherapy. 32:295, 1968. In this test protocol, acetic acid is administered to mice using an intraperitoneal route. The administered acetic acid induces a characteristic behavior consisting of a wave of constriction and elongation passing caudally along the abdominal wall. Analgesic agents cause a decrease in the number of writhing responses induced by acetic acid.

Using this acetic acid writhing test, Applicants have discovered that a weight ratio of 1:5 of oxycodone and dextromethorphan provides optimal efficacy. Applicants have found that oral administration of a dosage of X milligrams of oxycodone in combination with 5×milligrams of dextromethorphan provides about the same pain relief as does an oral dosage of 2×oxycodone. Thus for example, an oral dosage form which includes 5 milligrams of oxycodone in combination with 25 milligrams of dextromethorphan provides the same pain relief as does an oral dose of 10 milligrams of oxycodone alone.

Applicants have further found that use of lesser amounts of dextromethorphan, i.e. use of weight ratios lower than 1:5, does not maximally potentiate the oxycodone. On the other hand, use of greater amounts of dextromethorphan, i.e. use of weight ratios greater than 1:5, does not provide analgesic efficacy in excess of the 1:5 weight ratio.

In certain embodiments, step 420 further includes providing microcrystalline cellulose, such as for example Avicel PH 101, and dispersing that microcrystalline cellulose within the Actives Granulation. Avicel PH 101 is sold by FMC BioPolymer.

In certain embodiments, step 410 further includes providing carnuba wax, a carbomer, polyvinylpyrrolidone, magnesium stearate, and non-crystalline silicon dioxide, i.e. fumed silica, and dispersing those ingredients in Applicants' Actives Granulation. By "carbomer," Applicants mean a carboxyvinyl polymer, such as for example Carbopol 934 NF which meets the USP 26/NF 21 monograph for Carbomer 934.

In step 430, Applicants' method forms Applicants' Osmagen Granulation. Applicants' Osmagen Granulation provides a sustained release of the oxycodone/dextromethorphan combination over a period of between about 12 hours and about 24 hours, where that sustained release is not a function of pH. As those skilled in the art will appreciate, a sustained release oral dosage is exposed to fluids having a pH as low as 1.2 in the stomach, and thereafter to fluids having a pH greater than 7.0 in the intestinal tract. Using the USP Paddle Method, as described in the U.S. Pharmacopoeia XXII (1990), the difference between the amount of oxycodone and/or dextromethorphan released at pH 1.6 and the amount released at any other pH up to, and including, pH 7.2 is ten percent (10%) by weight or less.

Step 430 includes providing and mixing sodium carboxy methyl cellulose, sodium chloride, one or more carbomers, microcrystalline cellulose, iron oxide, magnesium stearate, and talc. These components of Applicants' Osmagen Granulation are blended, and then formed into 0.5 inch slugs. Those slugs are subsequently ground through an 18 mesh screen to form Applicants' Osmagen Granulation.

Figure 1A:
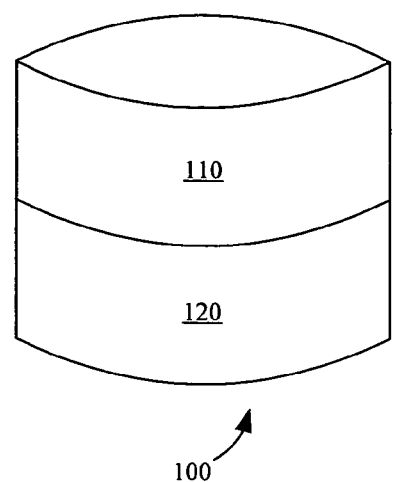
FIG. 1A is a perspective view of Applicants' bi-layer tablet.

In step 440, Applicants' method forms a bi-layer tablet. Referring now to FIG. 1A, bi-layer tablet 100 includes first layer 110 and second layer 120. In certain embodiments, bi-layer tablet is formed using a bi-layer press. In other embodiments, first layer 110 is formed separately from second layer 120, and those two layers are subsequently stacked to form bi-layer tablet 110. First layer 110 comprises Applicants' Actives Granulation prepared in step 420. Second layer 120 comprises Applicants' Osmagen Granulation prepared in step 430.

Figure 1B:
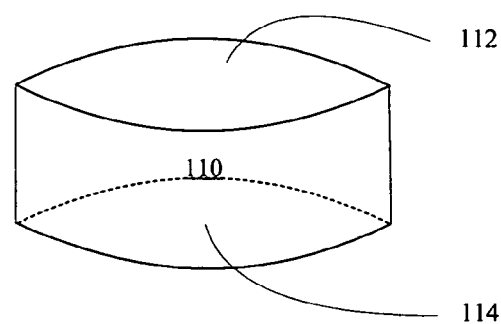
FIG. 1B is a perspective view of a first layer disposed in the tablet of FIG. 1A.
Figure 1C:
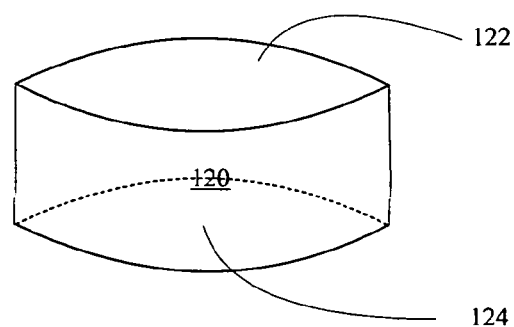
FIG. 1C is a perspective view of a second layer disposed in the tablet of FIG. 1A.

Referring now to FIG. 1B, first layer 110 includes first surface 112 and opposing second surface 114. Referring now to FIG. 1C, second layer 120 includes first surface 122 and opposing second surface 124. Referring to FIGS. 1A, 1B, and 1C, in bi-layer tablet 100, second surface 114 of first layer 110, i.e. the Actives Granulation layer, is in physical contact with first surface 122 of second layer 120. i.e. the Osmagen Granulation layer.

In step 450, Applicants' method provides an encapsulant. In certain embodiments, the encapsulant comprises polyethylene glycol. In certain embodiments, Applicants' encapsulant is formed from polyethylene glycol in combination with cellulose acetate. In certain embodiments, Applicants' encapsulant is formed using polyethylene glycol having a number average molecular weight of about 400 Daltons.

Figure 2:
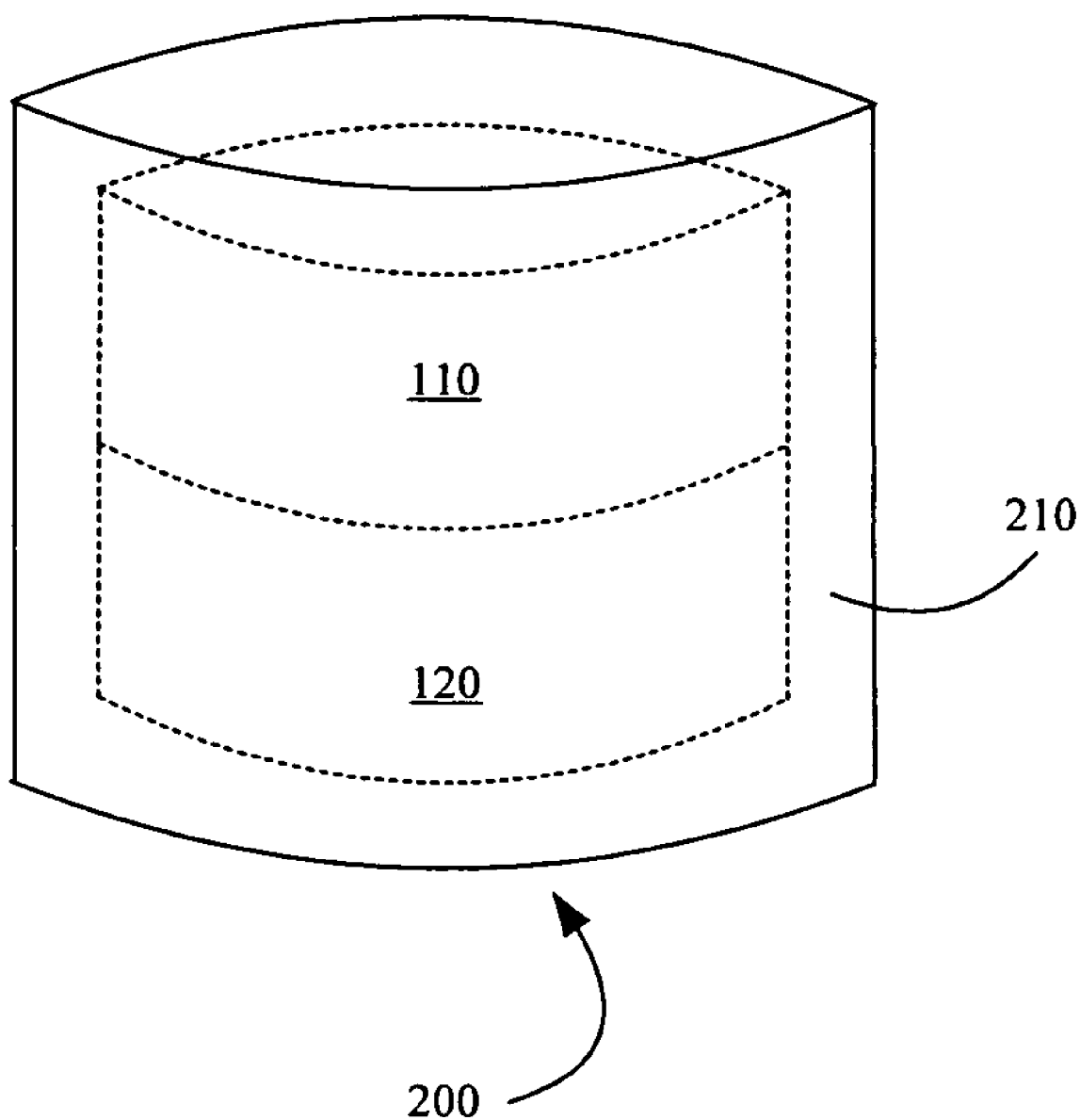
FIG. 2 is a perspective view of Applicants' encapsulated bi-layer tablet.

Referring now to FIG. 2, further in step 450 Applicants' method coats bi-layer tablet 100 with encapsulant 210 to form encapsulated bi-layer tablet 200. The dosage forms of the present invention may optionally be coated with one or more materials suitable for the regulation of release or for the protection of the formulation. In one embodiment, coatings are provided to permit either pH-dependent or pH-independent release, e.g., when exposed to gastrointestinal fluid. A pH-dependent coating serves to release the opioid in desired areas of the gastro-intestinal (GI) tract, e.g., the stomach or small intestine, such that an absorption profile is provided which is capable of providing at least about eight hours and preferably about twelve hours to up to about twenty-four hours of analgesia to a patient. When a pH-independent coating is desired, the coating is designed to achieve optimal release regardless of pH-changes in the environmental fluid, e.g., the GI tract. In certain embodiments, Applicants' oral dosage form includes compositions which release a portion of the oxycodone/dextromethorphan in one desired area of the GI tract, e.g., the stomach, and release the remainder of the oxycodone/dextromethorphan in another area of the GI tract, e.g., the small intestine.

Encapsulant 210 may be disposed over bi-layer tablet 100 using methods known to those skilled in the art, such as spraying, calendaring, immersion, and the like. Spray application can be carried out by pan coating or by use of a fluid bed, such as the Wurster fluidized bed.

Figure 3:
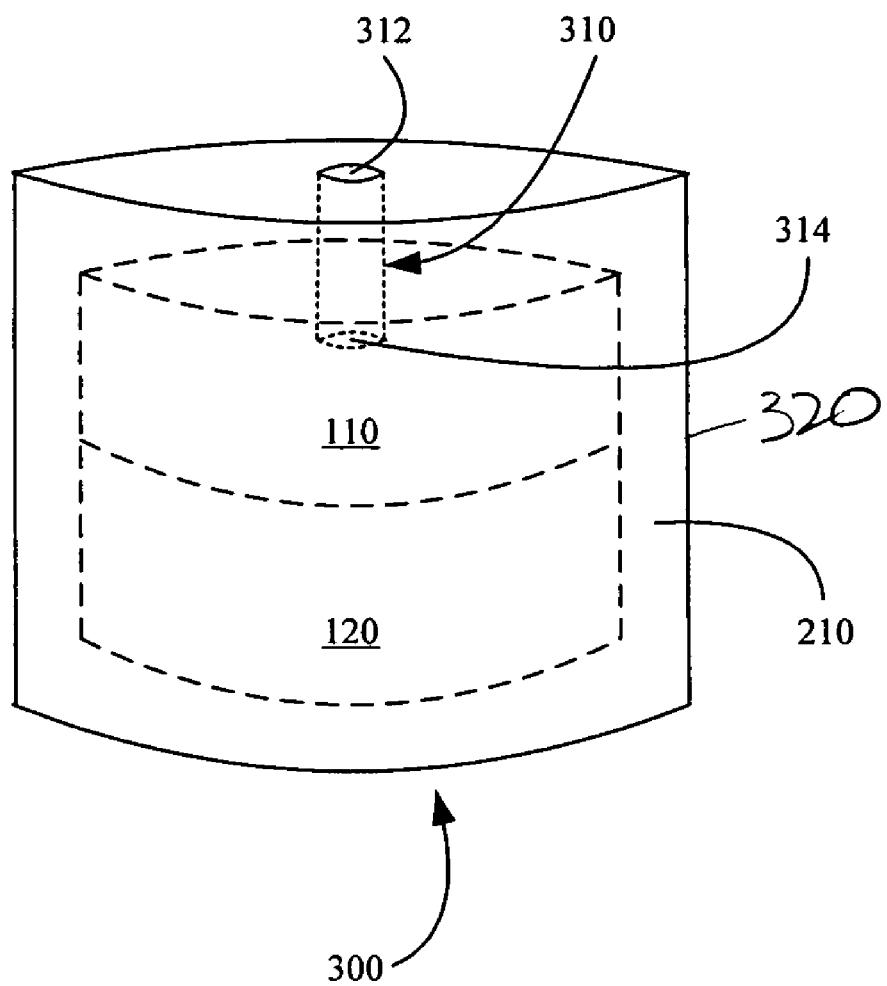
FIG. 3 is a perspective view of Applicants' oral dosage form.

Referring now to FIG. 3, the oral dosage form 300 of this embodiment includes outer surface 320. In step 460 Applicants' method forms an aperture extending through outer surface 320, through encapsulant 210, and into first layer 110. In certain embodiments, oral dosage form 300 is formed to include aperture 310 which interconnects first opening 312 in outer surface 320 and second opening 324 in first layer 110. The proximal portion of aperture 310 extends through encapsulant 210. The distal portion of aperture 310 extends into Actives Granulation layer 110.

The following examples are merely illustrative of the present invention and should not be considered limiting of the scope of the invention in any way. These examples and equivalents thereof will become more apparent to those skilled in the art in light of the present disclosure and the accompanying claims.

EXAMPLE I

This Example I describes Applicants' method to form an oral dosage form which comprises about 5 milligrams oxycodone and about 25 milligrams dextromethorphan.

A. Actives Granulation

Applicants formed the Actives Granulation of this Example by forming a first mixture consisting of about 0.2 grams of oxycodone HCl, about 1.0 grams of dextromethorphan HBr, about 0.6 grams of Avicel PH 101, and about 0.4 grams of Carnuba Wax. This first mixture was blended for about 10 minutes using a laboratory blender. Applicants' then formed a second mixture by adding about 2.5 grams of Carbopol 934 to the first mixture. The second mixture was blended for about 10 minutes.

Applicants formed a third mixture by adding about 2.4 grams of polyvinylpyrrolidone to the second mixture. The third mixture was blended for about 10 minutes. Applicants then formed a fourth mixture by adding about 0.1 grams of magnesium stearate to the third mixture. After blending the fourth mixture for about 5 minutes. Thereafter, the blended fourth mixture was formed into 0.5 inch slugs and ground through an 18 mesh screen.

Applicants' prepared a fifth mixture by adding added about 0.1 grams of magnesium stearate and about 0.1 grams of Cab-O-Sil to the blended/screened fourth mixture. This fifth mixture was blended for about 5 minutes. The blended fifth mixture comprised Applicants' Actives Granulation of this Example.

B. Osmagen Granulation

Applicants formed their Osmagen Granulation of this Example by forming a sixth mixture by combining about 3.0 grams of sodium carboxy methyl cellulose, about 2.0 grams of sodium chloride, about 2.0 grams of Carbopol 934, about 3.2 grams of Avicel PH 101, and about 0.7 grams of Iron oxide. This sixth mixture was blended for about 10 minutes using a laboratory blender.

Applicants then formed a seventh mixture by adding about 0.1 grams of magnesium stearate and about 0.1 grams of talc to the sixth mixture. This seventh mixture was blended for about 5 minutes. Applicants' Osmagen Granulation, comprising the blended seventh mixture, was formed into 0.5 inch slugs and then ground through an 18 mesh screen.

C. Bi-Layer Tablet

Applicants then used a bi-layer press outfitted with a 9/32 inch punch to form a tablet comprising a first layer which included 220 milligrams of the Actives Granulation described above, and a second layer which included 190 milligrams of the Osmagen Granulation.

D. Coating

Applicants prepared an encapsulant composition by mixing 40 parts of methylene chloride, 4 parts of cellulose acetate, and one part polyethylene glycol having a molecular weight of about 400 Daltons. The bi-layer tablet of this Example was repeatedly coated with Applicants' encapsulant composition until that encapsulant added about 15 weight percent to the weight of the bi-layer tablet. The coated tablets were then cured for four hours at 55° C.

E. Aperture

Thereafter, a hole was drilled through the encapsulant and into the first layer, i.e. the later comprising the Actives Granulation. In certain embodiments, the hole was formed using a laser device. In other embodiments, the hole was formed using a mechanical means, i.e. a drill.

EXAMPLE II

This Example II describes Applicants' method to form an oral dosage form which comprises about 9 milligrams oxycodone and about 45 milligrams dextromethorphan.

A. Actives Granulation

Applicants formed the Actives Granulation of this Example by forming a first mixture consisting of about 0.36 grams of oxycodone HCl, about 1.8 grams of dextromethorphan HBr, about 0.6 grams of Avicel PH 101, and about 0.4 grams of Carnuba Wax. This first mixture was blended for about 10 minutes using a laboratory blender. Applicants' then formed a second mixture by adding about 2.5 grams of Carbopol 934 to the first mixture. The second mixture was blended for about 10 minutes.

Applicants formed a third mixture by adding about 2.4 grams of polyvinylpyrrolidone to the second mixture. The third mixture was blended for about 10 minutes. Applicants then formed a fourth mixture by adding about 0.1 grams of magnesium stearate to the third mixture. After blending the fourth mixture for about 5 minutes. Thereafter, the blended fourth mixture was formed into 0.5 inch slugs and ground through an 18 mesh screen.

Applicants' prepared a fifth mixture by adding added about 0.1 grams of magnesium stearate and about 0.1 grams of Cab-O-Sil to the blended/screened fourth mixture. This fifth mixture was blended for about 5 minutes. The blended fifth mixture comprised Applicants' Actives Granulation of this Example.

B. Osmagen Granulation

Applicants formed their Osmagen Granulation by forming a sixth mixture by combining about 3.0 grams of sodium carboxy methyl cellulose, about 2.0 grams of sodium chloride, about 2.0 grams of Carbopol 934, about 3.2 grams of Avicel PH 101, and about 0.7 grams of Iron oxide. This sixth mixture was blended for about 10 minutes using a laboratory blender.

Applicants then formed a seventh mixture by adding about 0.1 grams of magnesium stearate and about 0.1 grams of talc to the sixth mixture. This seventh mixture was blended for about 5 minutes. Applicants' Osmagen Granulation, comprising the blended seventh mixture, was formed into 0.5 inch slugs and then ground through an 18 mesh screen.

C. Bi-Layer Tablet

Applicants then used a bi-layer press outfitted with a 9/32 inch punch to form a tablet comprising a first layer which included 220 milligrams of the Actives Granulation described above, and a second layer which included 190 milligrams of the Osmagen Granulation.

D. Coating

Applicants prepared an encapsulant composition by mixing 40 parts of methylene chloride, 4 parts of cellulose acetate, and one part polyethylene glycol having a molecular weight of about 400 Daltons. The bi-layer tablet of this Example was repeatedly coated with Applicants' encapsulant composition until that encapsulant added about 15 weight percent to the weight of the bi-layer tablet. The coated tablets were then cured for four hours at 55° C.

E. Aperture

Thereafter, a hole was drilled through the encapsulant and into the first layer, i.e. the later comprising the Actives Granulation. In certain embodiments, the hole was formed using a laser device. In other embodiments, the hole was formed using a mechanical means, i.e. a drill.

While the preferred embodiments of the present invention have been illustrated in detail, it should be apparent that modifications and adaptations to those embodiments may occur to one skilled in the art without departing from the scope of the present invention as set forth in the following claims.

We claim:

1. An oral dosage form, comprising:
   a bi-layer tablet consisting of a first layer having a first surface and an opposing second surface and a second layer having a first surface and an opposing second surface, wherein said second surface of said first layer physically contacts said first surface of said second layer;
   an encapsulant disposed over said bi-layer tablet;
   wherein said first layer comprises an orally therapeutically effective dose of oxycodone HCl in combination with dextromethorphan HBr, wherein the ratio of oxycodone HCl to dextromethorphan HBr is 1:5 by weight;
   wherein said second layer comprises carboxy methyl cellulose, sodium chloride, and iron oxide;
   wherein said oral dosage form is formed to include an aperture extending through said encapsulant and into said first layer;
   and wherein said oral dosage form does not include an opioid antagonist.

2. The oral dosage of claim 1, wherein said first layer comprises about 9 milligrams of oxycodone and about 45 milligrams dextromethorphan.

3. The oral dosage of claim 1, wherein said first layer comprises about 5 milligrams of oxycodone and about 25 milligrams dextromethorphan.

4. The oral dosage of claim 3, further comprising polyvinylpyrrolidone dispersed in said first layer.

5. The oral dosage of claim 4, further comprising:
   a carbomer disposed in both said first layer and said second layer;
   magnesium stearate disposed in both said first layer and said second layer; and
   microcrystalline cellulose disposed in both said first layer and said second layer.

* * * * *